United States Patent [19]

Glenn

[11] 4,098,273
[45] * Jul. 4, 1978

[54] INHALATION DEVICE

[75] Inventor: Albert S. Glenn, Los Angeles, Calif.

[73] Assignee: Syntex Puerto Rico, Inc., Humacao, P.R.

[*] Notice: The portion of the term of this patent subsequent to Feb. 1, 1994, has been disclaimed.

[21] Appl. No.: 739,168

[22] Filed: Nov. 5, 1976

Related U.S. Application Data

[63] Continuation-in-part of Ser. No. 540,918, Jan. 13, 1975, Pat. No. 4,005,711.

[51] Int. Cl.² ............... A61M 15/06; A61M 15/08
[52] U.S. Cl. ................................. 128/206; 128/266; 222/193
[58] Field of Search ............ 128/266, 206, 207, 208, 128/265, 198, 199, 200, 201, 185; 222/193, 82 R, 83 R

[56] References Cited

U.S. PATENT DOCUMENTS

| | | | |
|---|---|---|---|
| 2,507,702 | 5/1950 | Fields | 128/206 |
| 2,549,303 | 4/1951 | Friden | 128/206 |
| 2,659,517 | 11/1953 | Reinhardt, Jr. | 222/82 |
| 3,507,277 | 4/1970 | Altounnyan et al. | 128/206 |
| 4,005,711 | 2/1977 | Glenn | 128/206 |
| 4,013,075 | 3/1977 | Cocozza | 128/208 |
| 4,014,336 | 3/1977 | Mathes | 128/206 |

*Primary Examiner*—Robert W. Michell
*Assistant Examiner*—Henry J. Recla
*Attorney, Agent, or Firm*—Tom M. Moran

[57] ABSTRACT

A breath actuated inhalation device having a housing having a passageway for the passage of air therethrough. The passageway, of relatively small diameter, opens into an emptying chamber, of relatively greater diameter, adjacent that end of the housing which is adapted for insertion into the mouth or nose of the user. Adjacent that end of the emptying chamber closest to the passageway, the device has means for receiving and opening a unit dose of powdered medicament for administration. During inhalation, a portion of the air stream passing through the passageway into the emptying chamber is deflected by a beveled deflector causing sufficient air flow to come into contact with the powdered medicament whereby the powdered medicament is entrained in the air stream being inhaled, and is carried into the nose, throat or lungs of the user where beneficial or therapeutic action of the medicament occurs.

34 Claims, 7 Drawing Figures

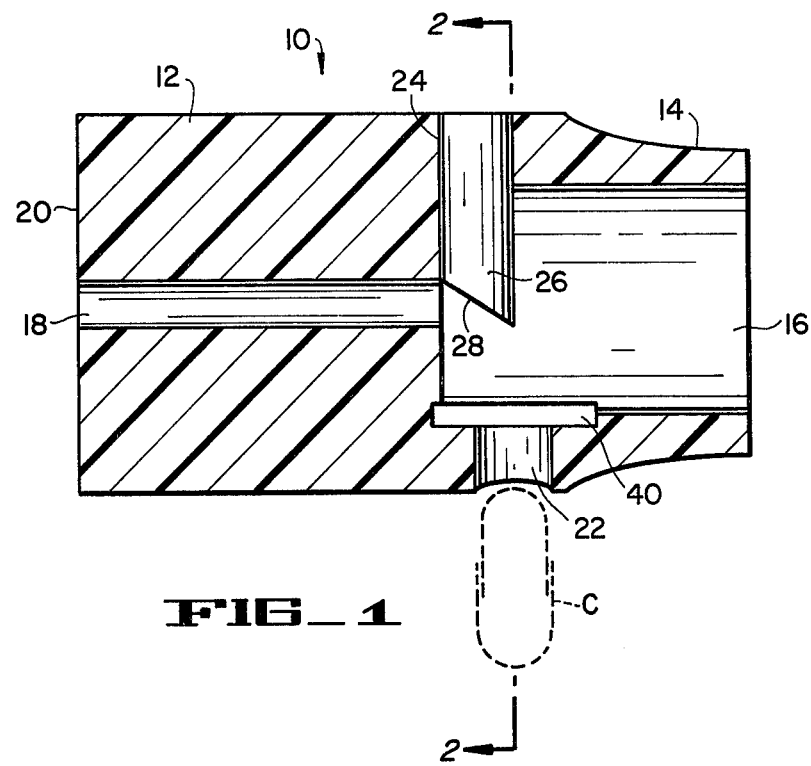
FIG_1
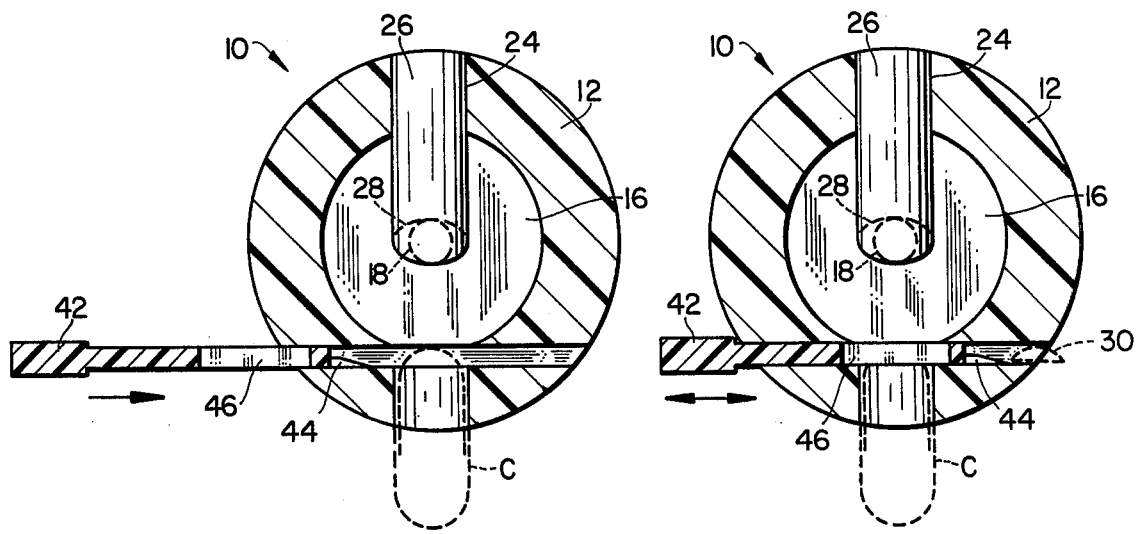
FIG_2   FIG_3

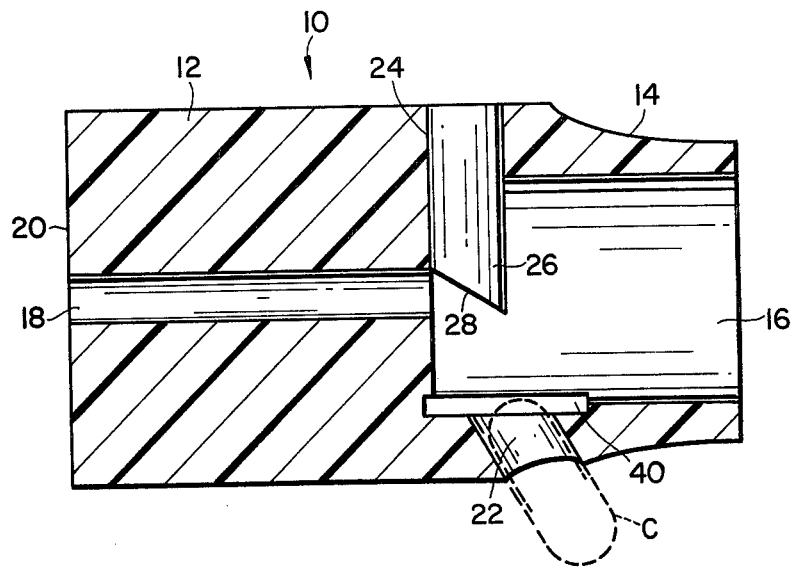
FIG_3
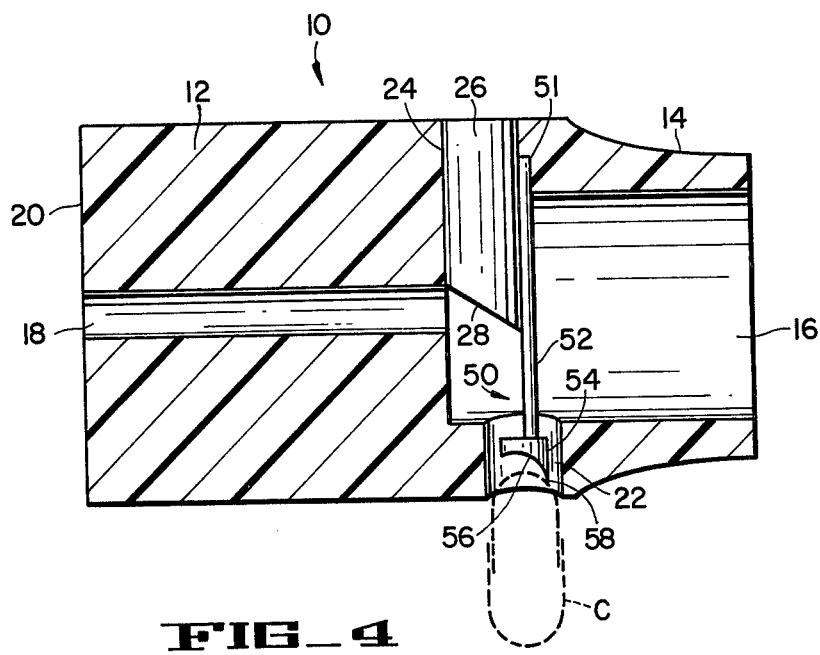
FIG_4

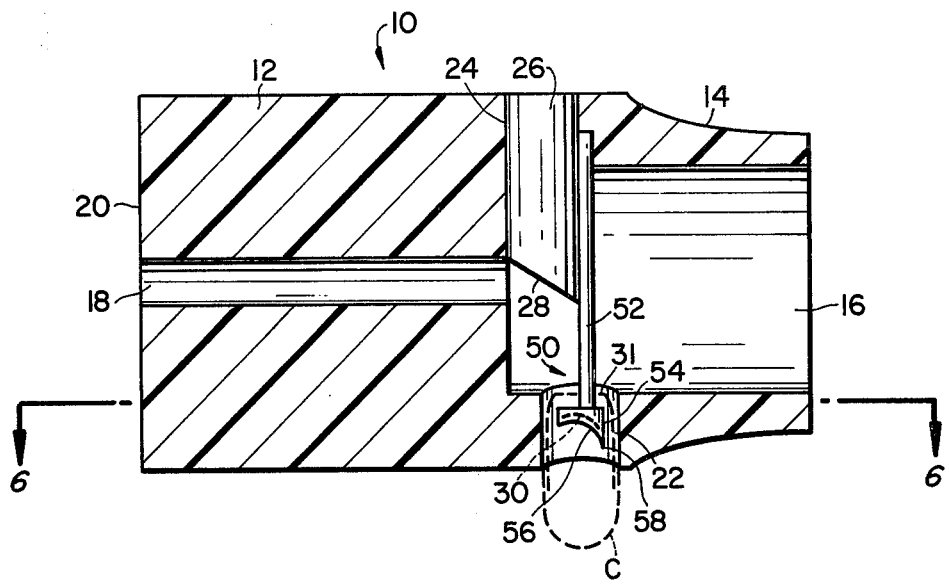
FIG_5
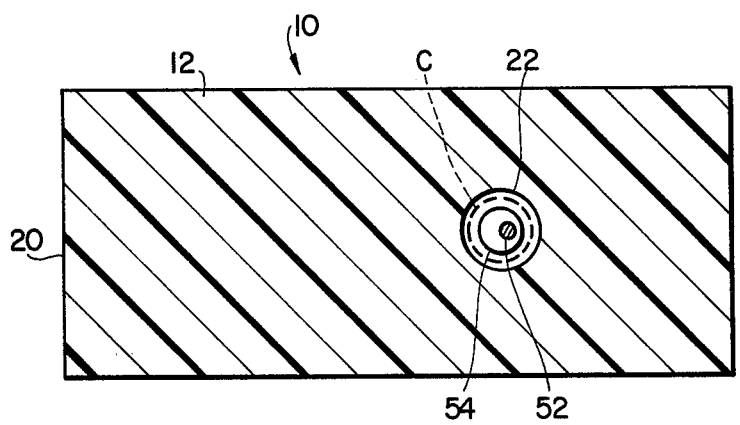
FIG_6

INHALATION DEVICE

REFERENCE TO PARENT APPLICATION

This application is a continuation-in-part of U.S. application Ser. No. 540,918 filed Jan. 13, 1975 now U.S. Pat. No. 4,005,711, issued Feb. 1, 1977.

FIELD OF THE INVENTION

This invention is related to breath actuated devices for the administration of powdered medicaments by inhalation. More particularly, this invention relates to an inhalation device having, in the essential aspects thereof, no parts which move while it is being used for medicament delivery, yet which is capable of causing a powdered medicament, held within a container inserted into the device, to be rapidly and effectively dispensed from the container, entrained in the air stream being inhaled and, thusly, carried into the nose, throat or lungs of the user where beneficial action of the medicament occurs. Incorporated in the device is a means to open the container of medicament as or after it is inserted into the device.

BACKGROUND OF THE INVENTION

Known, prior air inhalation devices include, for example, those shown in U.S. Pat. Nos. 988,352; 2,507,702; and 2,603,216; and Great Britain Pat. No. 1,118,431.

SUMMARY OF THE INVENTION

The breath actuated inhalation devices of the present invention include a housing having a passageway for the passage of air therethrough, one end of the housing being adapted for insertion into the mouth or nose of a user. The passageway, of relatively small diameter, opens into an emptying chamber, of relatively greater diameter, adjacent the output end of the housing. Adjacent that end of the emptying chamber closest to the passageway, the housing includes means for receiving or presenting a unit dose of powdered medicament for administration. As shown, this means is a port adapted to receive and hold a powdered medicament-holding container which is opened by an opening means as or after the container is inserted into the port. A beveled deflector is disposed adjacent but opposite the means for holding the container and, during inhalation, a portion of the air stream passing along the passageway into the emptying chamber is deflected by the beveled deflector into the container holding the medicament, whereby the powdered medicament in the container is entrained in the air stream being inhaled, and is carried into the nose, throat or lungs of the user where beneficial or therapeutic action of the medicament occurs. The medicament will be deposited in either the nose, throat or lungs depending upon the nature and size of the medicament particles and the embodiment of the device used to administer the medicament (e.g., a device with a mouthpiece will be utilized for administration of medicaments to the lungs, etc.).

In one embodiment, the axes of the deflector and the container port are off-set, with the axis of the deflector being closer to the passageway, to divert a portion of the air flow along the passageway into the medicament-holding capsule. The off-set distance (along the longitudinal axis of the device) is, in part, determined by the diameter of the passageway, the air flow rate through the device (as determined by the lung capacity and lung strength of the user), the angle of the beveled surface makes with the long axis of the deflector and the distance between the lower edge of the deflector and the upper edge of the container. However, by appropriate selection of the design parameters, the axes need not be off-set, it being adequate if the deflector diverts a portion of the air flow sufficient to empty the medicament holding container. In addition, the container port can be tilted (up to 30° from the vertical) toward the passageway (i.e., away from the output end of the housing) to further assist in causing the powdered medicament to be expelled from the container. All such design parameters can be varied singly or in combination to achieve desired medicament administration.

Container, as used herein, is intended to include any means by which a unit dose of medicament is presented to the device for administration. Capsules are the presently preferred form of containers; however, it is contemplated that other forms would be equally suitable if appropriate structural modifications of the device, to accommodate the different carrier, are made as, and if, necessary.

It has been found that, with the inhalation devices of this invention, the powdered medicament held within the container is rapidly and efficiently entrained in the air stream passing through the device during inhalation, and, as such, is carried into the nose, throat or lungs of the user for beneficial action of the medicament to occur.

BRIEF DESCRIPTION OF THE DRAWINGS

The foregoing and still further features and advantages of the present invention will become more apparent from the following detailed description, taken together with the accompanying drawings wherein:

FIG. 1 is a vertical cross-sectional view of one embodiment of an inhalation device of the present invention which has a channel for means for opening a medicament-holding container after it is inserted into the device;

FIG. 2 is a cross-sectional view of the device of FIG. 1 taken along line 2—2 of FIG. 1 showing the opening means in the position before the medicament-holding container has been opened;

FIG. 3 is a cross-sectional view of the device of FIG. 1 taken along line 2—2 of FIG. 1 showing the opening means in the position after the medicament-holding container has been opened.

FIG. 4 is a vertical cross-sectional view of an alternate embodiment of the inhalation device of the present invention which has means for opening a medicament-holding container as it is inserted into the device, FIG. 4 showing the container prior to being opened;

FIG. 5 is the same view as FIG. 4 except that the medicament holding container is open;

FIG. 6 is a top view along horizontal line 6—6 in FIG. 5; and

FIG. 7 is a vertical cross-sectional view similar to FIG. 1 except that the container part is tilted toward the passageway.

FURTHER DISCUSSION OF THE INVENTION AND PREFERRED EMBODIMENTS

In the discussion below, reference will be made to a capsule as the exemplary medicament-holding container for presenting the medicament to the device for administration. As set forth above, other containers are contemplated for use with the device described herein. In the ensuing discussion of the various figures, like numerals are utilized to represent like elements.

Referring to FIG. 1, there is shown an inhalation device 10 having a housing 12 which is preferably cylindrical (as can best be seen in FIG. 2). At one end of housing 12 is a mouthpiece 14 intended for insertion into the mouth of a user thereof. Mouthpiece 14 can be redesigned to permit insertion into the nasal passages or, if desired, an adapter (not shown) can be placed over the mouthpiece to permit nasal use. Adjacent mouthpiece 14 is an emptying chamber 16 connected at the inner end thereof to passageway 18 which extends through to the other end 20 of the device. The manner of connecting passageway 18 with chamber 16 can be squared-off as shown, or more streamlined, if desired, as long as the particular configuration selected is effective to cause the powdered medicament to be expelled from the capsule during the desired number of inhalations. If desired, passageway 18 can initiate in an incoming or entrance chamber (not shown) of similar dimension and configuration to emptying chamber 16. Adjacent the lower, inner end of chamber 16 and extending through the wall of housing 12, there is an opening or port 22 into which capsule C, as shown in the dotted outline in FIG. 1, is inserted prior to inhalation.

Opposite port 22 there is a cylindrical passageway 24 in which there is inserted a beveled deflector 26. Optionally, the deflector can be fabricated directly as part of a unitary-type device. Deflector 26 has a beveled or slanted surface 28 which deflects a portion of the air stream passing through the device during inhalation into port 22. The deflector can be inserted from different positions as long as a sufficient portion of the air stream is deflected into the capsule to cause the powdered medicament to be dispensed therefrom. Upon inhalation, the air passing through the device, including the portion deflected in the port 22 where a capsule C opened as described hereinafter is located. The deflected air promptly and effectively causes the powdered medicament to be expelled from the capsule, entrained in the air stream passing through the device and, as such, carried into the throat or lungs of the user for beneficial or therapeutic action thereof to occur.

Incorporated into the inhalation device is a means to open the medicament-holding capsule C either after it is inserted into the container receiving means, i.e., port 22, as shown in FIGS. 1 - 3 and 7 or as it is inserted into the container receiving means as shown in FIGS. 4 - 6.

Referring first to FIGS. 1 - 3, the inhalation device shown therein has a channel 40 extending substantially transversely to the longitudinal axis, and thus passageway 18, of the device.

Slide 42 movable within channel 40 has a sharp blade 44 fixedly secured to the leading edge thereof. After partial insertion of unopened capsule C into port 22, the slide is moved laterally to slice open the top of the capsule and thereby expose the medicament to be administered, the severed part 30 of the capsule being preferably ejected out of the device through the far end of channel 40. The capsule can be left as shown in FIG. 2 during inhalation, or, preferably, pushed further up in port 22 through opening 46 in slide 42, or slide 42 can be withdrawn, with or without further upward movement of the capsule. In this manner, the capsule is opened after insertion into the device and the contents thereof exposed for administration. Air is drawn through passageway 18 and a part thereof is deflected downwardly from deflector surface 28 to force medicament from the opened capsule.

Referring now to FIGS. 4–6, the inhalation device with a means to open the capsule as it is inserted into port 22 is set forth. Directly opposite port 22 and extending below beveled face 28 is an opening means 50 which preferably includes an arm 52 fixedly attached opposite port 22 which is imbedded in a portion 51 of the mouthpiece 14 so that it is stationary relative to the movement of capsule C. Alternatively, arm 52 may be affixed to beveled deflector 26 as a unitary part of the deflector. Arm 52 terminates in a lower portion 54 having a sharp edge 56 and a point 58. In horizontal cross-section as shown in FIG. 6 as viewed downwardly at line 6—6 it can be seen that lower portion 54 is circular and forms a downwardly facing hollow, beveled-walled cylinder. As the capsule C is inserted into port 22, the top thereof will come into contact with point 58 and edge 56 whereby, upon continued movement of the capsule, a hole (designated in FIG. 5 by flattened area 31) will be created in the capsule, the top 30 of the capsule being retained in the cylindrical shaped part of lower portion 54. During inhalation, air drawn through air stream tube 18 is directed into the opened capsule and assists in causing the medicament to be expelled from the capsule through the annular space between the exterior surface of the arm 52 and the adjacent edge of the hole cut in the top of the capsule by the lower edge of the tube, which, as shown in FIG. 5, is sufficiently below the top of the capsule but above the level of medicament to permit expulsion of the powdered medicament through the annular space.

In still a further modification of the device of this invention shown in FIG. 7, the port 22 may be tilted (up to 30° from the vertical) towards passageway 18 (i.e., away from the output end of the housing) to further assist in causing the powdered medicament to be expelled from the container. Numerals in FIG. 7 which are common to FIG. 1 are intended to designate like elements of the inhalation device.

Whether the capsule C is opened after insertion into the device or as it is inserted into the device, the operation is essentially the same. Once the capsule is in port 22 and opened, the mouthpiece is then taken into the mouth and, upon inhalation, part of the air flowing through passage 18 is deflected by surface 28 and causes the medicament to be expelled from the capsule and entrained in the air stream flowing through the emptying chamber 16. In this manner, the medicament is carried into the throat or lungs of the user for beneficial or therapeutic action to occur.

The entire device can be made of metal but preferably is made of suitable plastic material, such as nylon, polyacetal or polypropylene. With the exception of the capsule or other medicament-holding container and the opening means, the device in its basic elements, is preferably of unitary construction, although multi-piece construction is contemplated, especially where the deflector is separately provided. The beveled deflector is also preferably made from plastic, such as from those referred to above. The device of this invention can be manufactured quite readily, thereby effecting substantial cost reduction in the manufacturing process, without adversely affecting medicament administration during inhalation.

The physical properties of each medicament formulation (i.e., the ability to fluidize and the flow characteristics thereof) will affect the ease or manner in which it is dispensed with these or other inhalation devices. However for a given powdered formulation, varying the diameter of passageway 18, the positioning of port 22 (from the position as shown toward the open end of chamber 16), the angle of the beveled surface, the depth to which the deflector extends above or below the longitudinal axis of passageway 18, the height above the inside of emptying chamber 16 to which the medicament-holding container extends, and/or, in general, modification of the overall configuration and shape of chamber 16 and passageway 18, the devices can be made to deliver the medicament in a different number of inhalations or in a longer or shorter period of time, depending upon the nasal or lung capacities and strengths of each particular user. Quite obviously, no single device will be optimal for all persons requiring administration of powdered medicaments since, for example, people with differing lung capacities and strengths are known to generate flow rates from about 30 liters/minute or so to about 120 liters/minute or so through inhalation devices of this and known types. Nonetheless, the devices of this invention afford such variability through proper selection of the various design parameters listed above, that a device, embraced within the scope of this invention, can be designed for a particular patient-generated flow rate to deliver the medicament according to a certain set of pre-determined objectives (e.g., slow or fast administration, one or more inhalations, etc.). The net result is that a family of devices, all embraced within the present invention, can be designed, each of which will deliver the medicament under a different, given set of selected administration conditions. Conversely, the devices of this invention can be designed to cover an extensive range of operating conditions and thus be suitable for use by a variety of persons having differing inhalation abilities or capacities.

While the present invention has been described with reference to specific embodiments thereof, it will be understood by those skilled in this art that various changes may be made and equivalents may be substituted without departing from the true spirit and scope of the invention. Additionally, other modifications may be made to adapt a particular situation, material or composition of matter, structural desirability, or then-present objective to the spirit of this invention without departing from its essential teachings.

What is claimed is:

1. A breath-actuated inhalation device for dispensing a medicament from a medicament-holding container comprising a housing having a passageway for the movement of air therethrough, one end of said housing being an output end adapted for insertion into the mouth or nasal passages of a user thereof; said passageway terminating in an emptying chamber adjacent the output end of said housing, the cross-sectional area of said passageway being less than the cross-sectional area of said emptying chamber; a first opening extending through a wall of said housing and opening into said emptying chamber for receiving a medicament-holding container; means to open said medicament-holding container as it is inserted into said first opening; and deflector means extending into said emptying chamber adjacent the interface thereof with said passageway for deflecting a portion of the air being drawn through said passageway during inhalation into the opened medicament-holding container whereby the medicament held therein is dispensed therefrom.

2. The device of claim 1 wherein said container opening means comprises a sharp, enlarged point on the end of an arm fixedly attached opposite said first opening, said sharp point serving to open a closed medicament-holding container as the container is inserted into said first opening said sharp, enlarged point extending into the opened medicament-holding container held in said first opening during inhalation to a point above the level of the medicament therein but below the top of the container whereby, during inhalation, the medicament is dispensed from the container through the space defined by the outer surface of said arm and the inner surface of the opening in the top of the container.

3. The device of claim 1 wherein the longitudinal axis of said first opening is tilted toward said passageway at an angle up to about 30° from the vertical.

4. The device of claim 1 wherein said deflector means comprises a second opening in said housing adjacent said emptying chamber, and a deflection member having a beveled surface at the end thereof closest to said first opening, said beveled, surface facing the direction of air flow through said passageway and serving to deflect a portion of the air being drawn through said passageway during inhalation toward said first opening.

5. The device of claim 4 wherein said second opening is opposite said first opening.

6. The device of claim 4 wherein said deflection member is movable within said second opening.

7. The device of claim 4 wherein the longitudinal axis of said second opening is off-set from the longitudinal axis of said first opening, the axis of said first opening being closer to the output end of said housing than is the axis of said second opening.

8. The device of claim 1 wherein said deflector means comprises a deflection member having a beveled surface at the end thereof closest to said first opening, said beveled surface facing the direction of air flow through said passageway during inhalation and serving to deflect a portion of the air being drawn through said passageway during inhalation toward said first opening.

9. The device of claim 8 wherein the plane of said beveled surface is at an angle of about 30° to about 60° with the longitudinal axis of said deflection member.

10. The device of claim 9 wherein the longitudinal axis of said first opening is tilted toward said passageway at an angle up to about 30° from the vertical.

11. A breath-actuated inhalation device for dispensing a medicament from a medicament-holding container comprising a housing having a passageway for the movement of air therethrough, one end of said housing being an output end adapted for insertion into the mouth or nasal passages of a user thereof; said passageway terminating in an enlarged emptying chamber adjacent the output end of said housing, the cross-sectional area of said passageway being less than the cross-sectional area of said emptying chamber; a first opening extending through a wall of said housing and opening into said emptying chamber for receiving a medicament-holding container; means to open said medicament-holding container as it is inserted into said first opening; deflector means extending into said emptying chamber adjacent the interface thereof with said passageway for deflecting only a portion of the air being drawn through said passageway into said first opening during inhalation, said deflector means comprising a deflection member having a beveled surface at the end thereof closes to said first opening, said beveled surface facing the direction of air flow through said passageway during inhalation, the plane of said beveled surface being an an angle of about 30° to about 60° with the longitudinal axis of said deflection member, said beveled surface serving to deflect an only portion of the air being drawn through said passageway into said first opening so that medicament is dispensed from the opened medicament-holding container held within said first opening.

12. The device of claim 11 where said first opening is tilted toward said passageway at an angle up to about 30° from the vertical.

13. The device of claim 11 wherein said deflection member is positioned within a second opening in said housing.

14. The device of claim 13 wherein said deflection member is movable within said second opening.

15. The device of claim 11 wherein the longitudinal axis of said second opening is off-set from the longitudinal axis of said first opening, the axis of said first opening being closer to the output end of said housing than is the axis of said second opening.

16. The device of claim 11 wherein said means to open the medicament-holding container is for opening said container as it is inserted into said container receiving first opening and comprises a sharp, enlarged point on the end of an arm fixedly attached opposite said first opening, said sharp point serving to open a closed medicament-holding container as the container is inserted into said first opening said sharp, enlarged point extending into the opened medicament-holding container held in said first opening during inhalation to a point above the level of the medicament therein but below the top of the container whereby, during inhalation, the medicament is dispensed from the container through the space defined by the outer surface of said arm and the inner surface of the opening in the top of the container.

17. The device of claim 11 wherein said opening means comprises a channel extending substantially transversely to said passageway through said housing at a point adjacent said first opening, and a slide movable in said channel, said slide having a sharp leading edge whereby, when said slide is pushed against the top of a medicament-holding container held within said first opening, the top of the container is sliced open to thereby expose the medicament therein.

18. The device of claim 17 wherein said slide further includes an opening therein adapted to be positioned between said deflector means and the opened, medicament-holding container when said slide has been moved to the position where the top of the medicament-holding container has been opened to expose the medicament therein.

19. A breath-actuated inhalation device for dispensing a medicament from a medicament-holding container comprising a housing having a passageway for the movement of air therethrough, one end of said housing being an output end adapted for insertion into the mouth or nasal passages of a user thereof; said passageway terminating in an emptying chamber adjacent the output end of said housing, the cross-sectional area of said passageway being less than the cross-sectional area of said emptying chamber; a first opening extending through a wall of said housing and opening into said emptying chamber for receiving a medicament-holding container; means to open said medicament-holding container after it is inserted into said first opening; and deflector means extending into said emptying chamber adjacent the interface thereof with said passageway for deflecting a portion of the air being drawn through said passageway during inhalation into the opened medicament-holding container whereby the medicament held therein is dispensed therefrom.

20. The device of claim 19 wherein said container opening means comprises a channel extending substantially transversely to said passageway through said housing at a point adjacent said first opening, and a slide movable in said channel, said slide having a sharp leading edge whereby, when said slide is pushed against the top of a medicament-holding container held within said first opening, the top of the container is sliced open to thereby expose the medicament therein.

21. The device of claim 20 wherein said slide further includes an opening therein adapted to be positioned between said deflector means and the opened, medicament-holding container when said slide has been moved to the position where the top of the medicament-holding container has been opened to expose the medicament therein.

22. The device of claim 19 wherein the longitudinal axis of said first opening is tilted toward said passageway at an angle up to about 30° from the vertical.

23. The device of claim 19 wherein said deflector means comprises a second opening in said housing adjacent said emptying chamber, and a deflection member having a beveled surface at the end thereof closest to said first opening, said beveled, surface facing the direction of air flow through said passageway and serving to deflect a portion of the air being drawn through said passageway during inhalation toward said first opening.

24. The device of claim 23 wherein said second opening is opposite said first opening.

25. The device of claim 23 wherein said deflection member is movable within said second opening.

26. The device of claim 23 wherein the longitudinal axis of said second opening is off-set from the longitudinal axis of said first opening, the axis of said first opening being closer to the output end of said housing than is the axis of said second opening.

27. The device of claim 19 wherein said deflector means comprises a deflection member having a beveled surface at the end thereof closest to said first opening, said beveled surface facing the direction of air flow through said passageway during inhalation and serving to deflect a portion of the air being drawn through said passageway during inhalation toward said first opening.

28. The device of claim 27 wherein the plane of said beveled surface is at an angle of about 30° to about 60° with the longitudinal axis of said deflection member.

29. The device of claim 28 wherein the longitudinal axis of said first opening is tilted toward said passageway at an angle up to about 30° from the vertical.

30. A breath-actuated inhalation device for dispensing a medicament from a medicament-holding container comprising a housing having a passageway for the movement of air therethrough, one end of said housing being an output end adapted for insertion into the mouth or nasal passages of a user thereof; said passageway terminating in an enlarged emptying chamber adjacent the output end of said housing, the cross-sectional area of said passageway being less than the cross-sectional areas of said emptying chamber; a first opening extending through a wall of said housing and opening into said emptying chamber for receiving a medicament-holding container; means to open said medicament-holding container after it is inserted into said first opening; deflector means extending into said emptying chamber adjacent the interface thereof with said passageway for deflecting only a portion of the air being drawn through said passageway into said first opening during inhalation, said deflector means comprising a deflection member having a beveled surface at the end thereof closest to said first opening, said beveled surface facing the direction of air flow through said passageway during inhalation, the plane of said beveled surface being at an angle of about 30° to about 60° with the longitudinal axis of said deflection member, said beveled surface serving to deflect an only portion of the air being drawn through said passageway into said first opening so that medicament is dispensed from the opened medicament-holding container held within said first opening.

31. The device of claim 30 where said first opening is tilted toward said passageway at an angle up to about 30° from the vertical.

32. The device of claim 30 wherein said deflection member is positioned within a second opening in said housing.

33. The device of claim 32 wherein said deflection member is movable within said second opening.

34. The device of claim 30 wherein the longitudinal axis of said second opening is off-set from the longitudinal axis of said first opening, the axis of said first opening being closer to the output end of said housing than is the axis of said second opening.

* * * * *